(12) United States Patent
Koudelka

(10) Patent No.: US 9,132,030 B2
(45) Date of Patent: Sep. 15, 2015

(54) THERAPEUTIC WRAP

(76) Inventor: Karen Koudelka, Fredericksburg, VA (US)

(*) Notice: Subject to any disclaimer, the term of this patent is extended or adjusted under 35 U.S.C. 154(b) by 325 days.

(21) Appl. No.: 12/976,556

(22) Filed: Dec. 22, 2010

(65) Prior Publication Data
US 2012/0165909 A1 Jun. 28, 2012

(51) Int. Cl.
A61F 7/02 (2006.01)
A61F 7/00 (2006.01)
A61F 7/10 (2006.01)

(52) U.S. Cl.
CPC ............ A61F 7/02 (2013.01); A61F 2007/0001 (2013.01); A61F 2007/023 (2013.01); A61F 2007/0207 (2013.01); A61F 2007/0219 (2013.01); A61F 2007/0238 (2013.01); A61F 2007/0242 (2013.01); A61F 2007/0268 (2013.01); A61F 2007/0279 (2013.01); A61F 2007/0298 (2013.01); A61F 2007/108 (2013.01)

(58) Field of Classification Search
USPC .......................... 607/112, 108, 114
See application file for complete search history.

(56) References Cited

U.S. PATENT DOCUMENTS

| 103,206 | A | 5/1870 | Dederick |
|---|---|---|---|
| D167,743 | S | 11/1951 | Dorfman |
| 3,312,987 | A | 4/1967 | Emery |
| 3,587,578 | A | 6/1972 | Walker |
| 3,900,035 | A | 8/1975 | Welch et al. |
| 4,055,188 | A | 10/1977 | Pelton |
| 4,516,564 | A | 5/1985 | Koiso et al. |
| 4,517,972 | A | 5/1985 | Finch, Jr. |
| 4,527,566 | A | 7/1985 | Abare |
| 4,556,055 | A | 12/1985 | Bonner, Jr. |
| 4,575,097 | A | 3/1986 | Brannigan et al. |
| 4,586,506 | A | 5/1986 | Nangle |
| 4,628,918 | A | 12/1986 | Johnson, Jr. |
| 4,628,932 | A | 12/1986 | Tampa |
| 4,669,476 | A | 6/1987 | Gordon et al. |
| 4,671,267 | A | 6/1987 | Stout |
| 4,706,658 | A | 11/1987 | Cronin |
| D294,650 | S | 3/1988 | De Beys |
| 4,802,667 | A | 2/1989 | Altner |
| 4,805,620 | A | 2/1989 | Meistrell |
| 4,860,748 | A | 8/1989 | Chiurco et al. |
| 4,886,063 | A | 12/1989 | Crews |
| 4,887,326 | A | 12/1989 | O'Brien et al. |
| 5,005,374 | A | 4/1991 | Spitler |
| D325,637 | S | 4/1992 | O'Brien et al. |
| 5,176,134 | A | 1/1993 | Hudson |
| 5,179,944 | A * | 1/1993 | McSymytz ................... 607/114 |
| D336,958 | S | 6/1993 | Pryor |
| D342,790 | S | 12/1993 | Zona |
| 5,300,104 | A | 4/1994 | Gaudreault et al. |
| 5,304,216 | A | 4/1994 | Wallace |
| D357,747 | S | 4/1995 | Kelly |
| 5,507,793 | A | 4/1996 | Hodges |
| D374,545 | S | 10/1996 | Cionni |
| 5,571,155 | A | 11/1996 | Bastille |

(Continued)

Primary Examiner — Michael Peffley
(74) Attorney, Agent, or Firm — Cooley LLP

(57) ABSTRACT

A therapeutic wrap includes a plurality of substantially rectangular chambers configured to receive a first amount of a thermoconductive material, and a plurality of substantially square chambers coupled to at least one of the substantially rectangular chambers, the square chambers configured to receive a second amount of a thermoconductive material. The substantially rectangular chambers and the substantially square chambers collectively define a substantially rectangular apparatus.

16 Claims, 7 Drawing Sheets

(56) References Cited

U.S. PATENT DOCUMENTS

| | | |
|---|---|---|
| D380,051 S | 6/1997 | Davis et al. |
| 5,728,146 A | 3/1998 | Burkett |
| 5,735,889 A | 4/1998 | Burkett |
| D403,778 S | 1/1999 | Davis et al. |
| D407,824 S | 4/1999 | Davis et al. |
| D408,923 S | 4/1999 | Davis et al. |
| 5,890,487 A | 4/1999 | Kimmel |
| D412,750 S | 8/1999 | Davis et al. |
| D413,168 S | 8/1999 | Davis et al. |
| 5,948,010 A | 9/1999 | Adamec |
| D417,006 S | 11/1999 | Davis et al. |
| D417,283 S | 11/1999 | Davis et al. |
| 5,984,953 A | 11/1999 | Sabin |
| D418,605 S | 1/2000 | Davis et al. |
| D418,606 S | 1/2000 | Davis et al. |
| D433,757 S | 11/2000 | Jordan |
| D436,179 S | 1/2001 | Small |
| D453,223 S | 1/2002 | Sherman |
| 6,699,271 B2 | 3/2004 | Clayton |
| 6,735,784 B2 | 5/2004 | Isom et al. |
| 2002/0052566 A1 | 5/2002 | Sequeira |
| 2003/0149461 A1* | 8/2003 | Johnson .................. 607/108 |

* cited by examiner

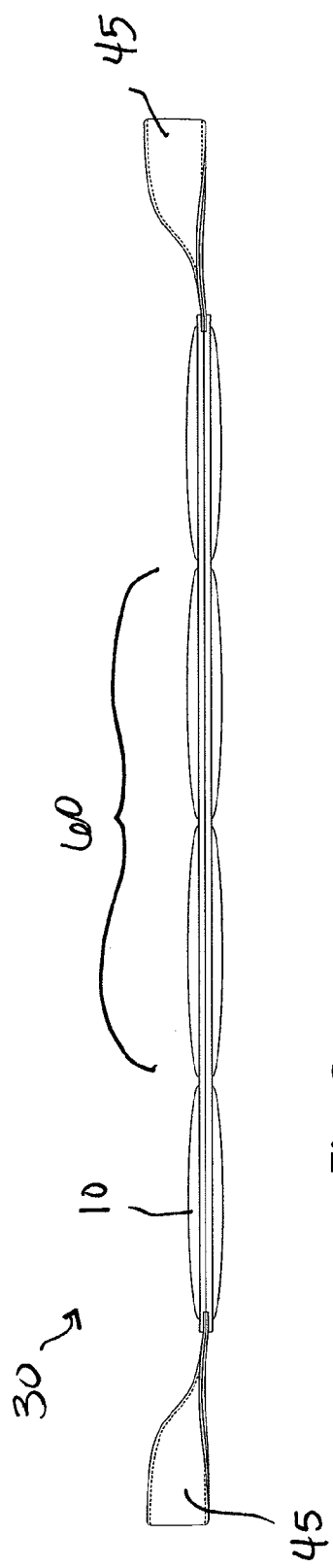
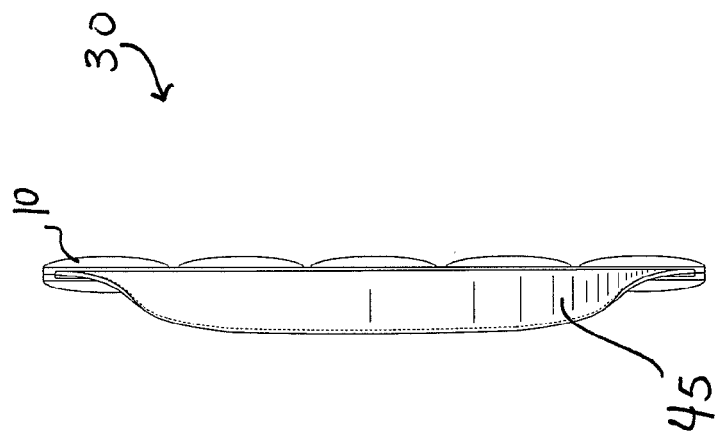
Fig. 3
Fig. 4

THERAPEUTIC WRAP

BACKGROUND

The invention relates generally to therapeutic wraps for thermal treatment of the human body.

It is known that the application of heat and/or cold to the body has not only many therapeutic benefits, but is also very relaxing to the individual to which it is administered.

Devices such as hot water bottles have been used for applying heat to the body, but such devices can become moist with condensation, and are not flexible enough to conform to the shape of the body. Additionally, heat retention is only maintained for a short period of time. Similar devices were used to apply cold to the body by filling a receptacle with ice cubes and/or chilled water. Such devices suffer similar shortcomings to the hot water bottle.

Other devices were developed over the years to overcome these shortcomings.

A suboccipital pillow for applying hot and/or cold treatments to the neck and the suboccipital areas of the body was developed. The pillow is generally of a crescent shape, one side of which is fitted with a lightly insulated pocket and the other side of which is fitted with a heavily insulated pocket into which crescent shape gel packs can be inserted after they are either heated or chilled.

Another device includes a temperature packet applied to the neck or shoulder of a user. The particular design of the temperature packet, however, does not provide enough surface area directly over the particular muscles to which heat or cold should be applied.

Known devices are not configurable to conform to multiple different body parts in multiple orientations. Accordingly, a need exists for such a device that can also include multiple receptacles to receive individual packets of thermoconductive material.

SUMMARY OF THE INVENTION

A therapeutic wrap conformable to various areas of the body is described herein. In one embodiment, the wrap includes a plurality of substantially rectangular chambers configured to receive a first amount of a thermoconductive material, and a plurality of substantially square chambers coupled to at least one of the substantially rectangular chambers. The square chambers are configured to receive a second amount of a thermoconductive material. The substantially rectangular chambers and the substantially square chambers collectively define a substantially rectangular apparatus that is conformable to multiple body parts.

BRIEF DESCRIPTION OF THE DRAWINGS

FIG. 3 is a side view of the therapeutic wrap according to an embodiment.

FIG. 4 is an end view of the therapeutic wrap according to an embodiment.

DETAILED DESCRIPTION

Figure 1:
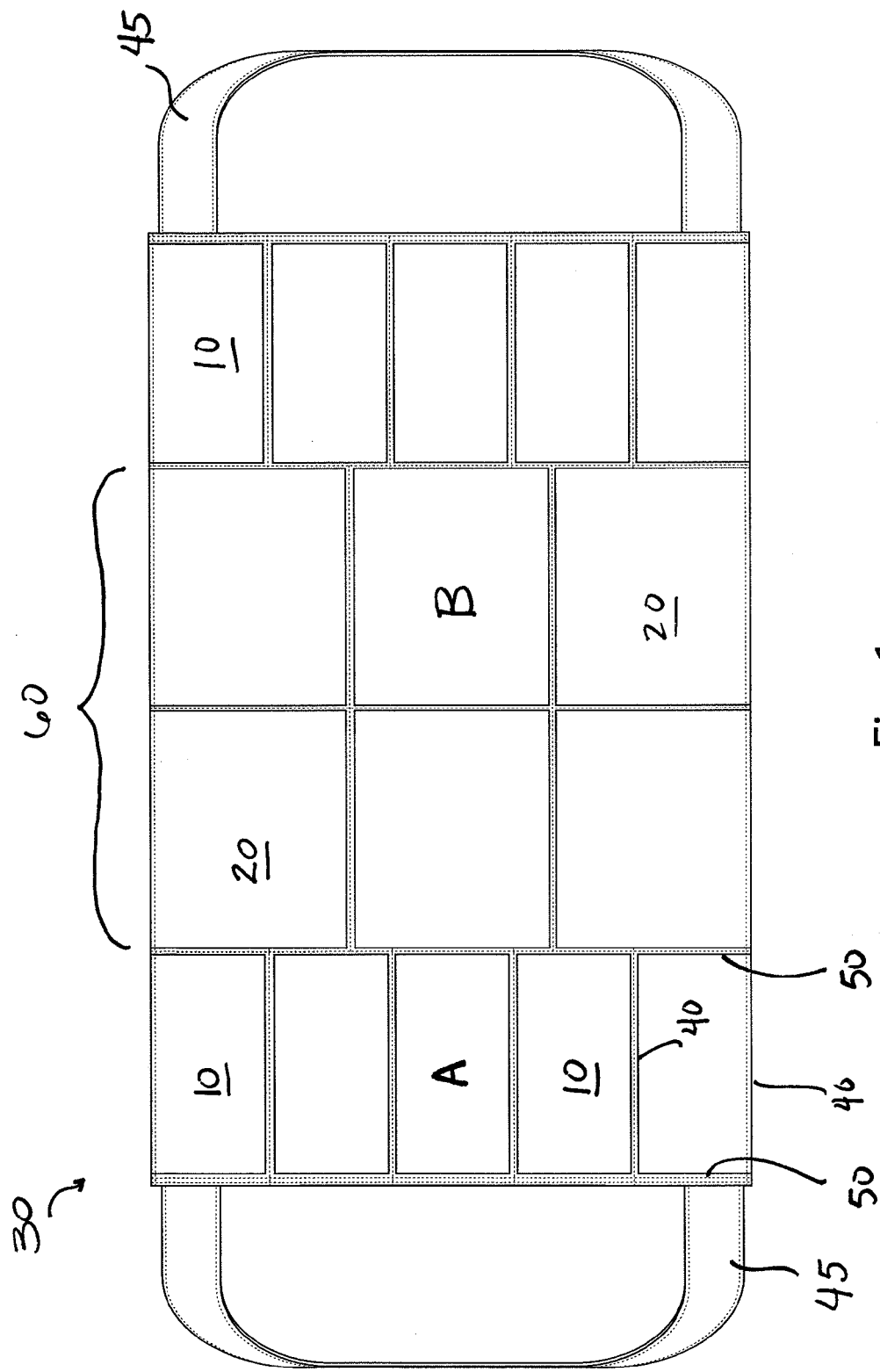
FIG. 1 is a top view of the therapeutic wrap according to an embodiment in a first configuration.

A therapeutic wrap conformable to various areas of the body is described herein. In one embodiment, the wrap includes a plurality of substantially rectangular chambers configured to receive a first amount of a thermoconductive (i.e., hot and cold) material, and a plurality of substantially square chambers coupled to at least one of the substantially rectangular chambers. The square chambers are configured to receive a second amount of a thermoconductive material. The substantially rectangular chambers and the substantially square chambers collectively define a substantially rectangular apparatus that is conformable to multiple body parts.

In some embodiments, an apparatus includes a plurality of rectangular chambers including a thermoconductive material disposed therein and a plurality of substantially square chambers including the thermoconductive material disposed therein. Each substantially rectangular chamber is attached on at least one edge to one of the other substantially rectangular chambers and is attached on only one edge to one of the substantially square chambers. Each substantially square chamber is attached on at least one edge to one or more of the other substantially square chambers and is attached on at most one edge to one of the substantially rectangular chambers.

In some embodiments, a therapeutic wrap includes a plurality of discrete volumes of thermoconductive material and a fabric portion defining a plurality of chambers configured to individually receive the discrete volumes of thermoconductive material. At least one area of the fabric portions contains a different number of chambers from at least one other area of the fabric portion. The plurality of chambers is arranged to form a symmetrical pattern movable between multiple configurations.

The therapeutic wrap is configured to be moved from a first, planar configuration to a second, substantially cylindrical configuration. In some embodiments, the therapeutic wrap is inserted in a sleeve to maintain the therapeutic wrap in the second configuration. In the first configuration, the therapeutic wrap is conformable to larger surface areas. When in the second configuration, the therapeutic wrap is configured to be draped, for example, over a user's neck.

FIGS. 1-4 illustrate a therapeutic wrap 30 in a first, planar configuration. The wrap 30 has substantially rectangular chambers 10 configured to receive a first amount of a thermoconductive material 33. Any thermoconductive material 33 may be used in conjunction with the wrap 30. For instance, the thermoconductive materials may be naturally derived material such as basmati rice or buckwheat, or chemically engineered material such as commercially available gel packs for heating and cooling. The wrap has substantially square chambers 20 that are coupled to the substantially rectangular chambers 10. The substantially square chambers 20 are also configured to receive thermoconductive material 33. Together, the substantially rectangular chambers 10 and the substantially square chambers 20 are configured as to form a substantially rectangular apparatus 30. As can be appreciated from FIG. 1, the substantially rectangular chambers and the substantially square chambers are configured in some embodiments to form a symmetrical pattern.

The volume of thermoconductive material 33 in the square chambers 20 may be the same as or different than the volume of thermoconductive material 33 in the rectangular chambers 10.

In some embodiments, the therapeutic wrap 30 includes handles 45 disposed on each end thereof. The handles 45 are useful in positioning the therapeutic wrap 30 in an appropriate location (e.g., on the user's back) or manipulating the therapeutic wrap in its various configurations as discussed in greater detail herein.

Figure 7A:
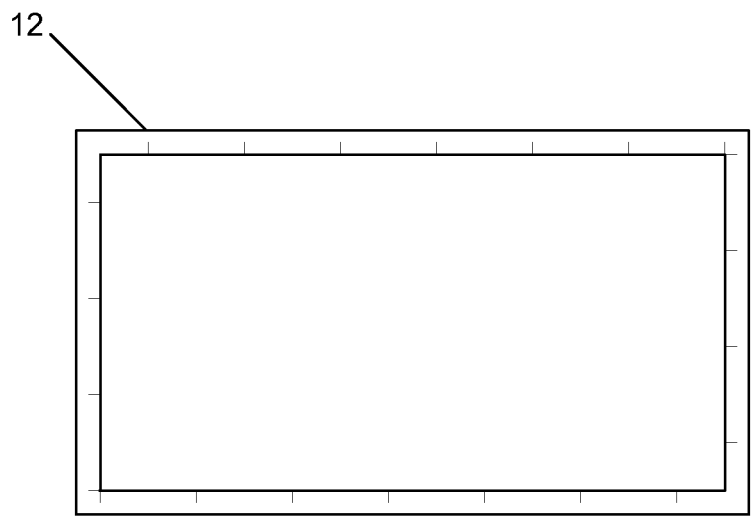
FIG. 7A is a top view of a pouch according to an embodiment.
Figure 7B:
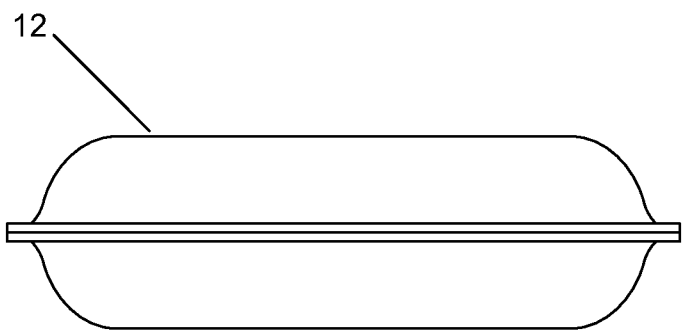
FIG. 7B is a side view of the pouch illustrated in FIG. 7A.
Figure 8A:
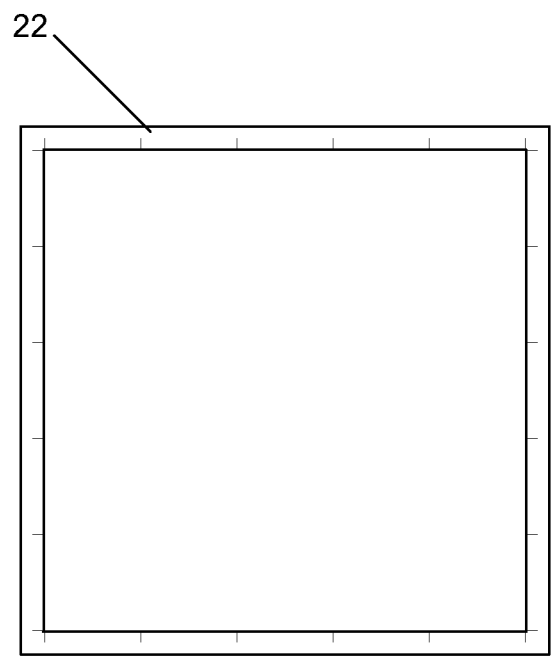
FIG. 8A is a top view of a pouch according to an embodiment.
Figure 8B:
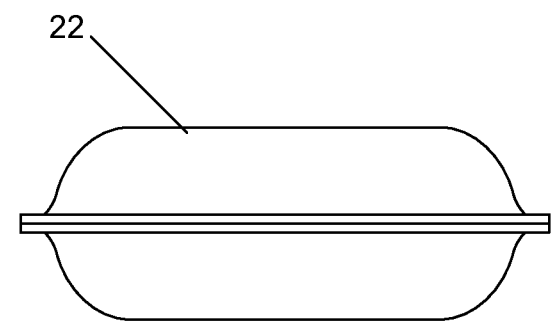
FIG. 8B is a side view of the pouch illustrated in FIG. 8A.

In some embodiments, the thermoconductive material 33 is contained within the chambers 10, 20, which can be lined or insulated to ensure the thermoconductive material 33 does not escape the chambers 10, 20 and/or migrate between adjacent chambers. In some embodiments, the thermoconductive material 33 is contained in separate pouches or packets (see, e.g., FIGS. 7A, 7B, 8A and 8B). FIG. 7A is a top view of a pouch 12 according to an embodiment, and FIG. 7B is a side view of pouch 12. FIG. 8A is a top view of a pouch 22 according to an embodiment, and FIG. 8B is a side view of pouch 22. The pouches can be configured to be substantially rectangular (FIGS. 8A and 8B) or substantially square (FIGS. 7A and 7B), so as to best fit the shape of the chamber into which it is to be inserted. The pouches of thermoconductive material can be removed from the wrap and placed in a freezer or other cooling device, or alternatively, into a microwave or other heating device, depending on whether the user wants to have a hot therapeutic wrap or a cold therapeutic wrap. Alternatively, some of the pouches may be cooled, while others are heated.

Due to their rectangular shape, the substantially rectangular chambers 10 have two long edges 40, and two shorter edges 50. In some embodiments, each substantially rectangular chamber 10 is coupled to at least one other substantially rectangular chamber 10 along one of the long edges 40 of the rectangular chambers 10. The substantially square chambers 20 are configured to be located in the central portion 60 of the therapeutic wrap 30, while the substantially rectangular chambers 10 are disposed adjacent to the sides of the central portion 60.

In some embodiments, the substantially rectangular chambers 10 are of a uniform size. In some embodiments, the substantially square chambers 20 are of a uniform size. In some embodiments, the long edge of the substantially rectangular chambers 10 are approximately the same length as one side of the substantially square chambers. While the therapeutic wrap 30 as illustrated includes ten rectangular chambers 10 and six square chambers 20, in some embodiments there are fewer square chambers 20 in the central portion 60 or more square chambers 20 in the central portion 60. In some embodiments, the therapeutic wrap 30 can have more or fewer rectangular chambers 10.

The square chambers 20 and rectangular chambers 10 of the wrap 30 can be configured in multiple ways. In some embodiments, each substantially rectangular chamber is attached on at least one edge to one of the other substantially rectangular chambers and is attached on only one edge to one or more of the substantially square chambers. For instance, as shown in FIG. 1, substantially rectangular chamber A is attached to two other substantially rectangular chambers, but is attached on only one edge to the substantially square chambers 20.

Similarly, in some embodiments, each substantially square chamber 20 is attached on at least one of its edges to one or more of the other substantially square chambers and is attached on at most one edge to one or more of the substantially rectangular chambers. For instance, as shown in FIG. 1, substantially square chamber B is attached to three other substantially square chambers, but is attached on only one edge to substantially rectangular chamber(s) 10.

Figure 2:
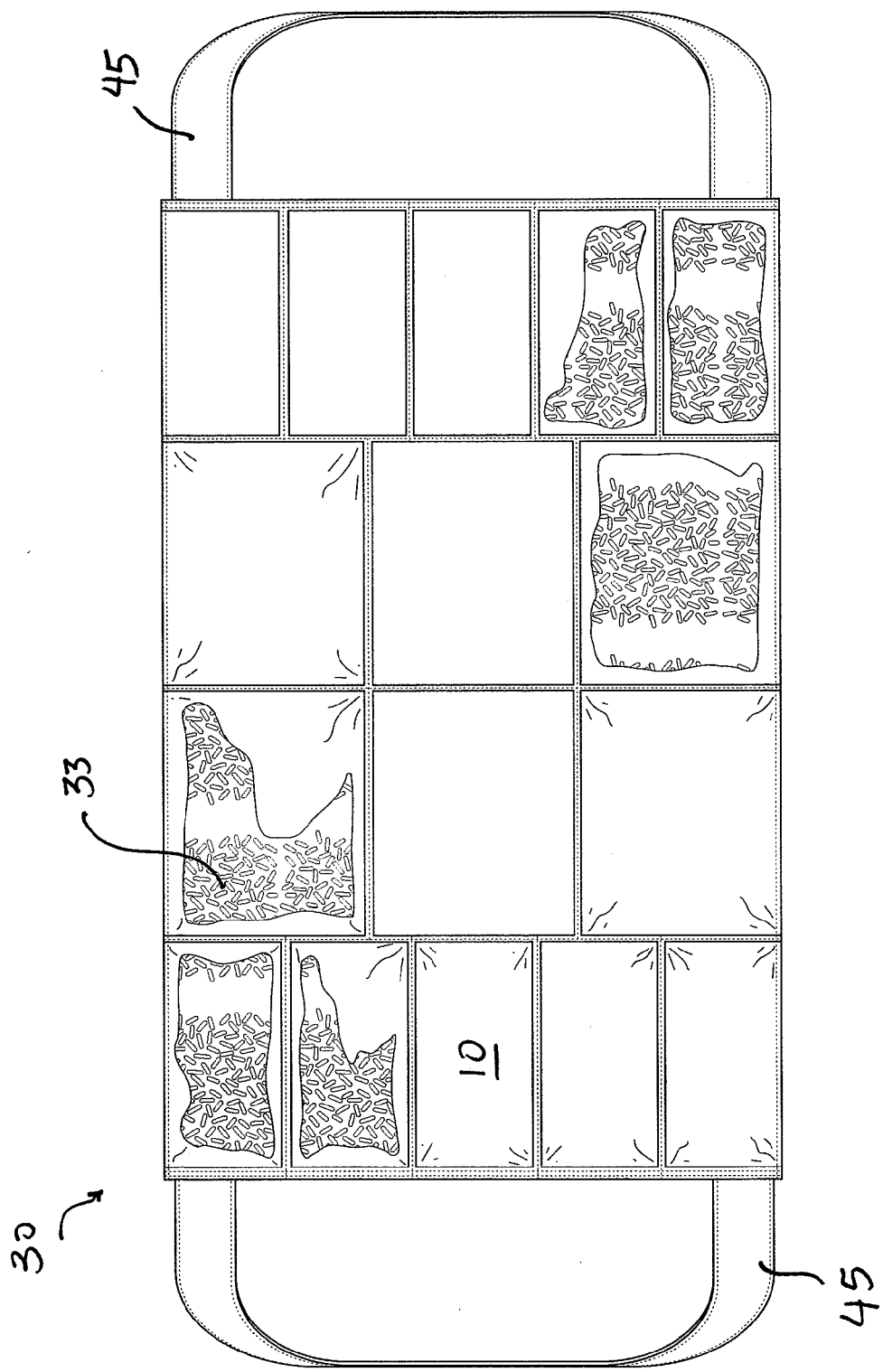
FIG. 2 is a partial cut-away of the therapeutic wrap illustrated in FIG. 1.

FIG. 2 illustrates a partial cut-away view of the therapeutic wrap 30. As illustrated in FIG. 2, the thermoconductive material 33 substantially fills the chamber 10, 20 in which it is situated. In some embodiments, a chamber 10, 20 may not be filled with any thermoconductive material. In such an embodiment, the chamber 10, 20 may be empty or can be filled with an insulating material. While the layers of material that make up the body of the therapeutic wrap are illustrated as conventional fabric, it should be understood that any type of fabric can be used. For example, semi-porous, absorbent, fabric can be used as well as a variety of other materials.

In some embodiments, the overall volume of thermoconductive material 33 is greater in the rectangular chambers 10 than in the central portion 60 (i.e., in the square chambers 20). In this manner, the central portion 60 of the therapeutic wrap 30 is more flexible (i.e., conformable) than the ends of the therapeutic wrap 30 with the rectangular chambers 10. Moreover, the increased weight of the ends of the therapeutic wrap 30 is useful in maintaining the therapeutic wrap 30 in its desired position and/or configuration.

Figure 5:
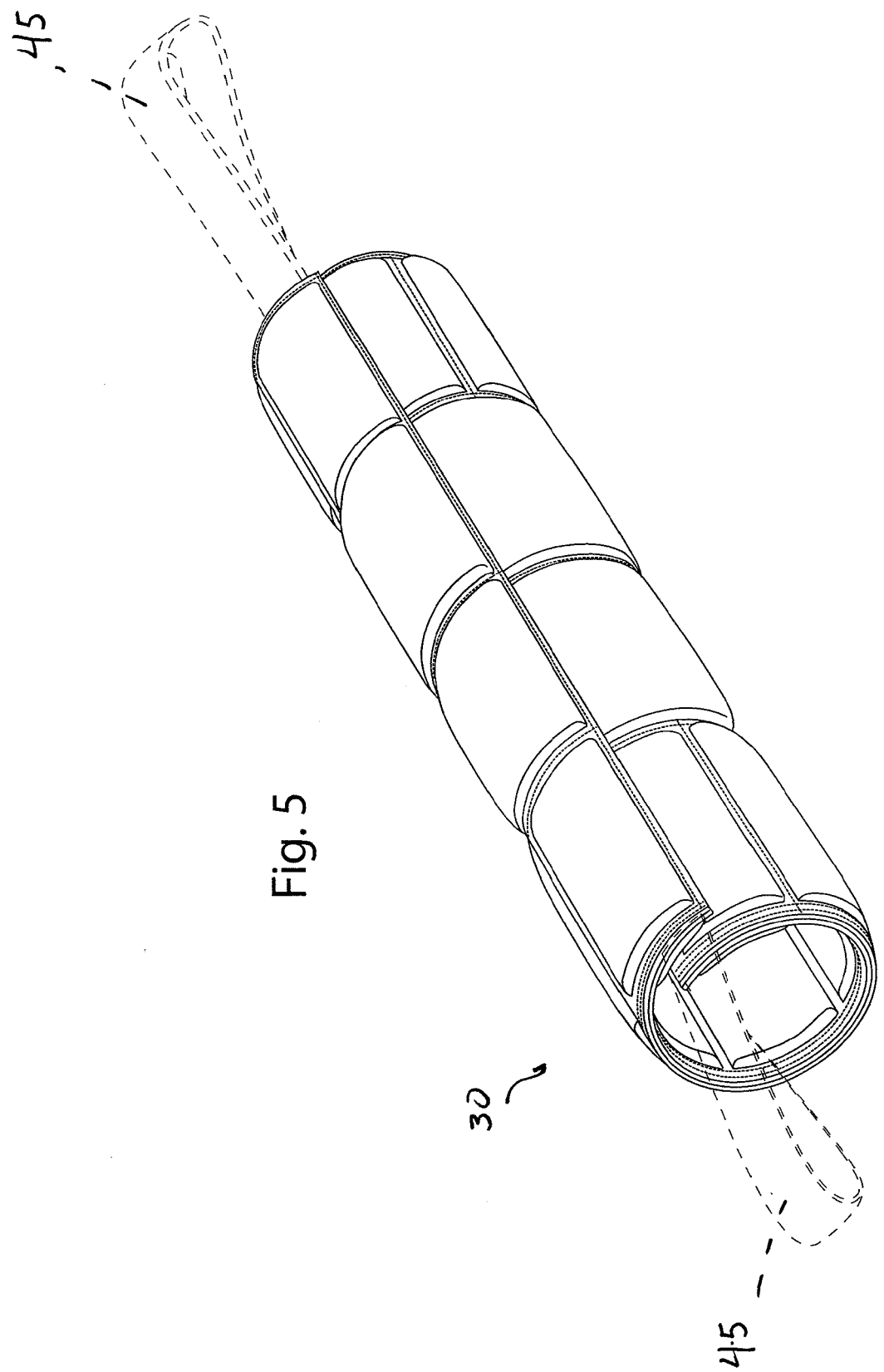
FIG. 5 is a perspective view of the therapeutic wrap according to an embodiment in a second configuration.
Figure 6:
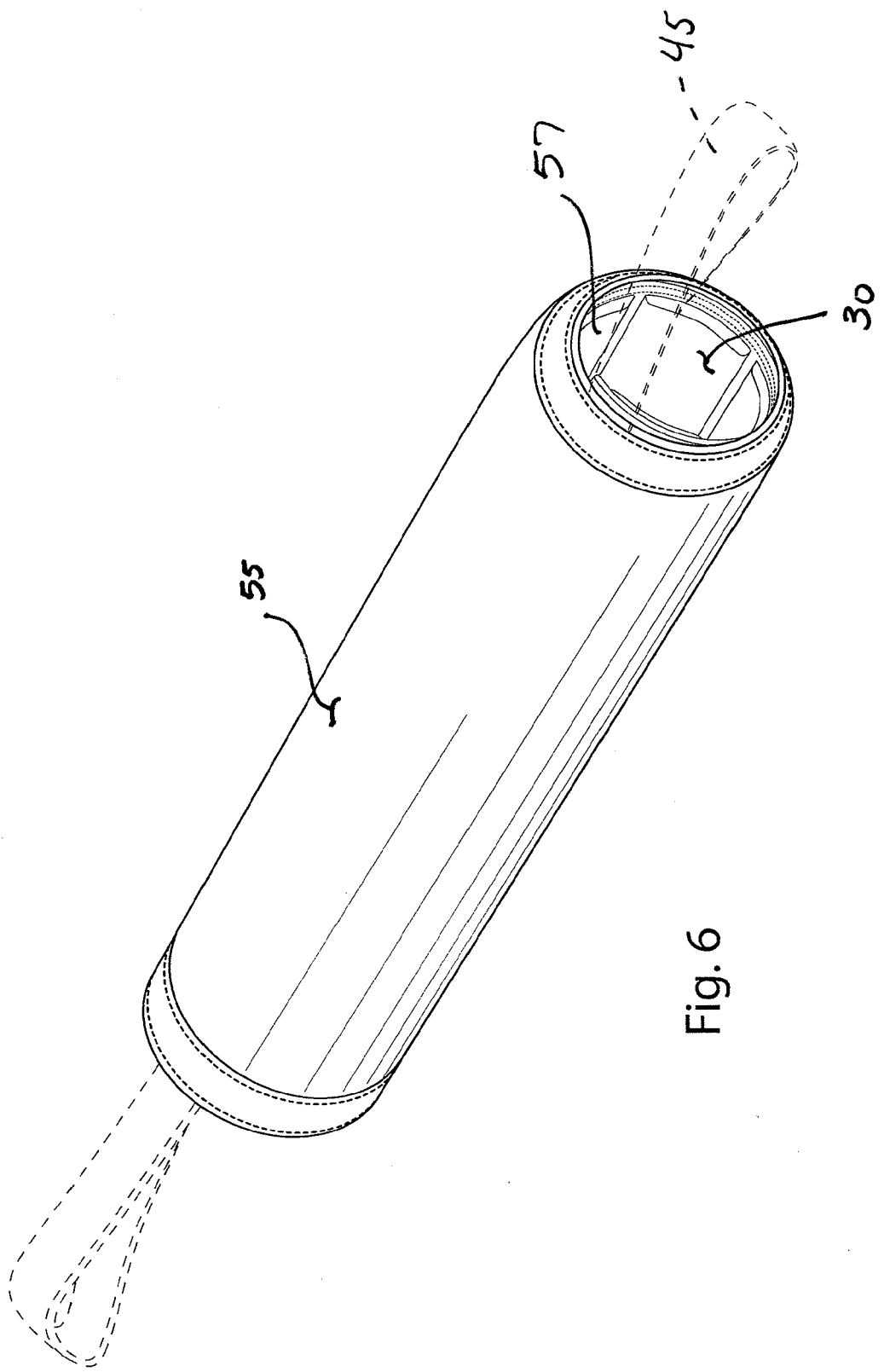
FIG. 6 is a perspective view of the therapeutic wrap according to an embodiment in the second configuration and inserted in a sleeve.

The therapeutic wrap 30 can be moved from its first, planar configuration (FIGS. 1-4) to a second, substantially cylindrical configuration as illustrated in FIGS. 5 and 6 by folding or rolling the therapeutic wrap. To maintain the therapeutic wrap 30 in its second configuration, it can be inserted into a separate sleeve 55. The sleeve 55 is substantially cylindrical and defines openings 57 in at least one of its ends such that a handle 45 of the therapeutic wrap 30 can extend therethrough. In some embodiments, as illustrated in FIG. 6, the sleeve 55 has openings 57 at both ends, thereby allowing the handles 45 to protrude therethrough.

In use, when the therapeutic wrap 30 is in its second configuration, whether in the sleeve 55 or not, a user can manipulate the handles to draw the rectangular portions downward such that the central portion substantially engages the neck (i.e., the therapeutic wrap is curved). In such a configuration and position, the weight of the rectangular portions can maintain the therapeutic wrap 30 in position such that it does not fall off the user's shoulders. Additionally, such a configuration and orientation (i.e., with the weight biasing the wrap 30 against the neck) promotes better temperature absorption.

Prior to use, the user can heat or cool the therapeutic wrap 30 depending on the desired effect. For example, the entire wrap 30 can be placed in the microwave, the oven, boiling water, a freezer, etc. such that it reaches a desired temperature. In some embodiments, the thermoconductive material in each of the chambers 10, 20 can have different thermoconductive properties such that each volume of thermoconductive material can cool and/or heat at different rates. In such a manner, for example, the portion adjacent the user's shoulders can cool off faster than the portion adjacent the neck.

In some embodiments, the chambers of the therapeutic wrap 30 are not unitarily formed and coupled; instead, the therapeutic wrap 30 has one or more fabric portions that define a plurality of chambers that are configured to individually receive discrete volumes of thermoconductive materials. The entire therapeutic wrap 30 may be made of one fabric portion or may be made of several fabric portions coupled together. Each fabric portion may have a plurality of chambers, and at least one area of the fabric portion or portions contains a different number of chambers from at least one other area of the fabric portion.

In some embodiments, the therapeutic wrap 30 is manufactured by stitching together two similarly sized pieces of fabric, defining pockets for receiving the thermoconductive material 33.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein.

For example, in an embodiment, each of the chambers 10, 20 can be the same size. In such an embodiment, the volume of thermoconductive material disposed in each of the chambers can be the same or different, depending on the desired characteristics of the device. For example, in some embodiments, the volume of thermoconductive material 33 can be smaller in the chambers in the central portion of the apparatus, while the volume of thermoconductive material 33 can be greater on the ends of the apparatus as described above.

The invention claimed is:

1. An apparatus comprising:
a plurality of substantially rectangular chambers configured to receive a first amount of a thermoconductive material, a first portion of the substantially rectangular chambers are disposed between a first side of a central portion of the apparatus and a first end of the apparatus, a second portion of the substantially rectangular chambers are disposed between a second side of the central portion and a second end of the apparatus, the first side of the central portion opposite the second side of the central portion, each substantially rectangular chamber from the plurality of substantially rectangular chambers has two longer edges and two shorter edges;
a plurality of substantially square chambers coupled to at least one of the substantially rectangular chambers, the substantially square chambers configured to receive a second amount of a thermoconductive material, the substantially square chambers located in the central portion, a portion of at least one substantially square chamber from the plurality substantially square chambers being longitudinally in line with a portion of at least one substantially rectangular chamber from the first portion of substantially rectangular chambers and with a portion of at least one substantially rectangular chamber from the second portion of substantially rectangular chambers;
a first handle disposed on the first end of the apparatus; and
a second handle disposed on the second end of the apparatus;
the plurality of substantially rectangular chambers and the plurality of substantially square chambers collectively defining a substantially rectangular apparatus having a longer edge and a shorter edge, the longer edges of each of the substantially rectangular chambers being parallel to the longer edge of the substantially rectangular apparatus.

2. The apparatus of claim 1, the apparatus further including the first amount of thermoconductive material and the second amount of thermoconductive material, wherein the first amount of thermoconductive material and the second amount of thermoconductive material are each a predetermined amount.

3. The apparatus of claim 1, the apparatus further including the first amount of thermoconductive material and the second amount of thermoconductive material, wherein the second amount of thermoconductive material is a different amount from the first amount of thermoconductive material.

4. The apparatus of claim 1, the apparatus further including the first amount of thermoconductive material and the second amount of thermoconductive material, wherein the first amount of thermoconductive material associated with each substantially rectangular chamber from the plurality of substantially rectangular chambers is contained in a pouch, the pouch configured to be inserted into each substantially rectangular chamber.

5. The apparatus of claim 1, the apparatus further including the first amount of thermoconductive material and the second amount of thermoconductive material, wherein the second amount of thermoconductive material associated with each substantially square chamber from the plurality of substantially square chambers is contained in a pouch, the pouch configured to be inserted into each substantially square chamber.

6. The apparatus of claim 1, wherein each substantially rectangular chamber is coupled to at least one other substantially rectangular chamber along one of the long edges of the substantially rectangular chambers.

7. The apparatus of claim 1, wherein the substantially rectangular chambers are a uniform size.

8. The apparatus of claim 1, wherein the substantially square chambers are a uniform size.

9. The apparatus of claim 1, wherein the length of a long edge of the substantially rectangular chambers is approximately the same as the length of one side of the substantially square chambers.

10. The apparatus of claim 1, wherein each substantially rectangular chamber is attached on at least one edge to one of the other substantially rectangular chambers and is attached on only one edge to one or more of the substantially square chambers.

11. The apparatus of claim 1, further comprising the first amount of thermoconductive material and the second amount of thermoconductive material, wherein a weight of the second amount of thermoconductive material being less than a weight of the first amount of thermoconductive material.

12. An apparatus comprising:
a plurality of first chambers including a thermoconductive material disposed therein, the plurality of first chambers located in a central portion of the apparatus, each first chamber from the plurality of first chambers being substantially square; and
a plurality of second chambers including the thermoconductive material disposed therein, each second chamber from the plurality of second chambers being substantially rectangular, a first portion of the plurality of second chambers located between a first side of the central portion and a first end of the apparatus and longitudinally in line with the central portion, a second portion of the plurality of second chambers located between a second side of the central portion and a second end of the apparatus opposite the first end of the apparatus and longitudinally in line with the central portion, a weight of an amount of thermoconductive material included in the first plurality of chambers being less than a weight of an amount of thermoconductive material included in the second plurality of chambers, each second chamber from the plurality of second chambers has two longer edges and two shorter edges;

wherein each first chamber is attached on at least one edge to one of the other first chambers and each first chamber is attached on only one edge to one of the second chambers; and wherein each second chamber is attached on at least one edge to one or more of the other second chambers and each second chamber is attached on at most one edge to one of the first chambers, wherein the plurality of first chambers and the plurality of second chambers collectively define a substantially rectangular apparatus having a longer edge and a shorter edge, the longer edges of each of the second chambers being parallel to the longer edge of the substantially rectangular apparatus.

13. The apparatus of claim 12, wherein the substantially rectangular chambers and substantially square chambers are configured to form a symmetrical pattern.

14. A therapeutic wrap comprising:
a body portion defining a plurality of chambers, at least one chamber from the plurality of chambers configured to receive a volume of a thermoconductive material;
a first handle coupled to a first end of the body portion; and
a second handle coupled to a second end of the body portion opposite the first end of the body portion,
the body portion having a first area including a first number of chambers and a second area having a second number of chambers, the first number of chambers being different from the second number of chambers, a first portion of the first area located between the first end of the body portion and a first side of the second area, a second portion of the first area located between the second end of the body portion and a second side of the second area opposite the first side of the second area, each chamber from the first number of chambers being substantially rectangular and having two longer edges and two shorter edges, each chamber from the second number of chambers being substantially square and having a length, a length of each of the longer edges of the first number of chambers being substantially the same length of each chamber from the second number of chambers, a portion of at least one substantially square chamber from the second number of chambers being longitudinally in line with a portion of at least one substantially rectangular chamber from the first portion of first area and with a portion of at least one substantially rectangular chamber from the second portion of the first area;
the body portion being movable between a first, planar configuration and a second, substantially cylindrical configuration;
the volume of the thermoconductive material is greater in the chambers in the second area than the volume of thermoconductive material in the first area.

15. The therapeutic wrap of claim 14, further comprising a sleeve configured to substantially surround the body portion when the body portion is in the second configuration, the sleeve defining an opening in at least one end thereof.

16. The therapeutic wrap of claim 14, further comprising:
a sleeve configured to substantially surround the body portion when the body portion is in the second configuration, the sleeve defining a first opening in at least one end thereof and a second opening in an opposite end thereof; and
the first handle configured to protrude through the first opening and the second handle configured to protrude through the second opening when the body portion is in the second configuration.

* * * * *